United States Patent [19]

McGregor

[11] 4,361,673
[45] Nov. 30, 1982

[54] POLYPEPTIDE COMPOSITIONS

[75] Inventor: William H. McGregor, Malvern, Pa.

[73] Assignee: American Home Products Corporation, New York, N.Y.

[21] Appl. No.: 286,138

[22] Filed: Jul. 27, 1981

Related U.S. Application Data

[63] Continuation-in-part of Ser. No. 188,804, Sep. 19, 1980, abandoned.

[51] Int. Cl.$^3$ .................. C07C 103/52; A61K 37/00
[52] U.S. Cl. ....................... 525/54.11; 260/112.5 R; 424/177
[58] Field of Search ............... 260/112.5 R; 424/177; 525/54.11

[56] References Cited

U.S. PATENT DOCUMENTS 4,250,086 2/1981 Heavner .................. 260/112.5 R

*Primary Examiner*—Delbert R. Phillips
*Attorney, Agent, or Firm*—George Tarnowski

[57] ABSTRACT

There are disclosed polypeptides having the formula:

$$R_1-Lys-Lys-X-R_2$$

wherein $R_1$ is hydrogen or p-Glu; X is Glu or Asp; and $R_2$ is Val, $NH_2$ or Val-$NH_2$; the fully protected peptide-resin intermediates thereof and pharmaceutically acceptable salts thereof. These polypeptides have the capability of inducing the maturation of T-cell populations and thus are useful in a number of therapeutic areas.

9 Claims, No Drawings

POLYPEPTIDE COMPOSITIONS

This is a continuation-in-part of Ser. No. 188,804, filed September 19, 1980, now abandoned.

BACKGROUND OF THE INVENTION

Recent research has established the involvement of the thymus in the functioning of the immune system in mammalian species. It is in the thymus that haemopoietic stem cells become differentiated to mature immunocompetent lymphocytes called T-cells, which circulate to the blood, lymph, spleen and lymph nodes. The T-cells have immunological specificity and are involved in the cell-mediated immune responses, such as graft responses, response to viral infections, response to neoplasms and so forth. The body's response to antigenic material, such as for example in response to bacterial attack, is the province of antibody secreting cells, called B-cells, which are derived from bone marrow stem cells, but which are not differentiated in the thymus. The antibody response to an antigen, in many cases, requires the presence of appropriate T-cells, so that T-cells, and consequently the thymus, are necessary for the body's immune system to make not only cellular immunity responses, but also humoral antibody response. The thymic induction of the necessary differentiation of stem cells to T-cells is mediated by secretions of thymic hormones by the epithelial cells of the thymus.

The great interest in thymic substances, which may be implicated in various aspects of the immune response, has been instrumental in creating a very productive research effort. As a result of this research, a number of thymic substances have been reported in the literature. In an article by Low et al. in *The Journal of Biological Chemistry*, volume 254, pages 981-993, 1979, there are disclosures regarding the potent immunopotentiating effect of the partially purified extract from thymus tissue termed thymosin Fraction 5. It has been shown that this thymosin fraction corrects some of the deficiencies resulting from lack of thymic function in a number of animal models, as well as in humans with primary immunodeficiency diseases and in immuno-suppressed cancer patients.

Further, in the Low et al. article, there is disclosed thay thymosin Fraction 5 is composed of several polypeptide components, two of which are designated thymosin $\alpha_1$ and polypeptide $\beta_1$. Of these two major components, thymosin $\alpha_1$ has been demonstrated to be a potent immunologically active thymic polypeptide, which is 10-1,000 times as active as the parent thymosin Fraction 5 when assayed in several biological models, including an in vivo mouse mitogen assay, an in vitro lymphokine assay measuring production of macrophage inhibitor factor (MIF), an in vitro induction of Lyt surface markers on putative T-cell precursors, and an in vitro human E-rosette assay measuring the production of T-cells.

The Low et al. article further establishes the sequence of the 28 amino acids comprising thymosin $\alpha_1$.

The present invention relates to short peptide sequences which have been found to exhibit characteristics of the long chain polypeptide isolated and named thymosin $\alpha_1$.

DESCRIPTION OF THE INVENTION

In accordance with this invention, there is provided a novel group of polypeptides having the structural formula:

wherein $R_1$ is hydrogen or p-Glu; X is Glu or Asp; and $R_2$ is Val, $NH_2$ or Val-$NH_2$, the fully protected peptide-resin intermediate thereof, and the pharmaceutically acceptable salts thereof.

In the depicted formula and throughout the specification and claims, where the chirality of an amino acid is not indicated or otherwise stated, it is understood to be of the L-series.

The fully protected peptide-resin intermediates, which comprise an additional aspect of the invention, may be depicted as follows:

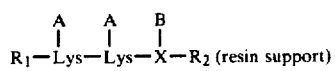

wherein $R_1$ and $R_2$ are as defined hereinbefore; and A and B are protecting groups which are hereinafter described. The intermediates comprise the fully protected polypeptide bound to a benzhydrylamine polystyrene resin support employed in the solid phase synthesis of the polypeptides.

The pharmaceutically acceptable salts of the compounds of the invention are those non-toxic addition salts produced by known methods from acids conventionally employed with pharmaceuticals such as hydrochloric, hydrobromic, sulfuric, phosphoric, polyphosphoric, maleic, acetic, citric, benzoic, succinic, malonic, ascorbic and the like.

The peptides of the invention are able to directly induce the maturation of T-cell populations, thereby affecting the very early stages of T-cell development. These effects are observable with concentrations as low as 1-100 ng/ml., making these compounds useful in the therapeutical treatment of a number of disorders of the immune response. Because the compounds perform certain of the thymic functions, they have application in various thymic function and immunity areas. Thus, the compounds can help to restore immune function and augment specific lymphocyte functions in children with hypothymic function and in adults with a variety of T-cell disorders, including cancer and autoimmune diseases. The polypeptides will increase or assist in therapeutic stimulation of cellular immunity and thereby become useful in the treatment of diseases involving chronic infection in vivo, such as fungal or mycoplasma infection, tuberculosis, leprosy, acute and chronic viral infections, and the like. Further, the compounds are useful in areas involving immunity deficiencies such as DiGeorge Syndrome, and in treating immunosuppressed cancer patients. The compounds may also be of therapeutic value in certain autoimmune diseases, such as systemic lupus erythematosus.

An important characteristic of the polypeptides is their in vivo ability to restore cells with the characteristic of the T-cells. The peptides are highly active in very low concentrations ranging from 1 nanogram per ml. up to 100 nanograms per ml. The carrier for the compounds may be any of the well known carriers for this purpose including normal saline solutions, preferably with a protein diluent such as bovine serum albumin to prevent adsorptive losses to glassware at these low concentrations.

The polypeptides are produced by the well known solid phase method as described by Stewart et al., *Solid Phase Peptide Synthesis*, Freeman and Co., San Francisco, 1969. As applied to some of the compounds of this invention, α-amino protected valine is attached to a benzhydrylamine polystyrene resin followed by removal of the α-amino protecting group with trifluoroacetic acid in methylene chloride, trifluoroacetic acid alone or HCl in dioxane. The deprotection is carried out at temperatures between about 0° C. and room temperature. Other standard cleaving reagents and conditions for removal of specific α-amino protecting groups may be used as described in Schroder and Lubke, "The Peptides", 1, 72–75 (Academic Press, 1965). After removal of the α-amino protecting group the subsequent protected amino acids are coupled individually to the resin supported sequence, seriatim. Alternatively, small peptide fragments may be prepared by the solution method and introduced into the solid phase reactor in about a four fold excess. The coupling is carried out in dimethylformamide, methylene chloride, or a mixture of the two solvents. The success of each coupling reaction at each stage of the synthesis is determined by the ninhydrin reaction as described by E. Kaiser et al., Analyt. Biochem., 34, 595 (1970). Where incomplete coupling has occurred, the reaction is repeated before the α-amino protecting group is removed for introduction of the next amino acid or amino acid sequence. The coupling reagent employed is diisopropylcarbodiimide.

After the desired amino acid sequence has been synthesized, the polypeptide is removed from the resin support by treatment with hydrogen fluoride and anisole to obtain the fully deprotected polypeptide. The polypeptide is then purified by one or more purification techniques, including gel filtration, high pressure preparative liquid chromatography and partition chromatograph.

The ultimate fully protected, resin bound polypeptides of this invention specifically exemplified are L-(5-oxoprolyl)-N$^\epsilon$-2-chlorobenzyloxycarbonyl-L-lysyl-N$^\epsilon$-2-chlorobenzyloxycarbony-L-lysyl-O-benzyl-L-glutamyl-L-valyl benzhydrylamine polystyrene amide; L-(5-oxoprolyl)-N$^\epsilon$-2-chlorobenzyloxycarbonyl-L-lysyl-N$^\epsilon$-2-chlorobenzyloxycarbonyl-L-lysyl-O-benzyl-L-glutamyl benzhydrylamine polystyrene amide; N$^\alpha$-t-butyloxycarbonyl-N$^\epsilon$-2-chlorobenzyoxycarbonyl-L-lysyl-N$^\epsilon$-2-chlorobenzyloxycarbonyl-L-lysyl-O-benzyl-L-glutamyl-L-valyl benzhydrylamine polystyrene amide; N$^\alpha$-t-butyloxycarbonyl-N$^\epsilon$-2-chlorobenzyloxycarbonyl-L-lysyl-N$^\epsilon$-2-chlorobenzyloxycarbonyl-L-lysyl-O-benzyl-L-aspartyl-L-valyl benzhydrylamine polystyrene amide; and N$^\alpha$-2-t-butyloxycarbonyl-N$^\epsilon$-2-chlorobenzyloxycarbonyl-L-lysyl-O-benzyl-L-glutamyl-L-valyl hydroxymethyl polystyrene ester.

The protecting groups employed throughout the solid phase synthesis are well known to the art. The α-amino protecting groups employed with each amino acid introduced in sequence of the ultimate polypeptide are of the following (1) acyl type protecting groups illustrated by the following: formyl, trifluoroacetyl, phthalyl, p-toluenesulfonyl(tosyl), nitrophenylsulfenyl, etc.; (2) aromatic urethane type protecting groups illustrated by benzyl oxycarbonyl and substituted benzyloxycarbonyl such as p-chlorobenzyloxycarbonyl, p-nitrobenzyloxycarbonyl, p-bromobenzyloxy carbonyl, p-methoxybenzyloxycarbonyl; (3) aliphatic urethane protecting groups illustrated by tert-butyloxycarbonyl, diisopropylmethoxycarbonyl, isopropyloxycarbonyl allyloxycarbonyl, 2,2,3-trichloroethoxycarbonyl, amyloxycarbonyl; (4) cycloalkyl urethane type protecting groups illustrated by cyclopentyloxycarbonyl, adamantyloxycarbonyl, cyclohexyloxycarbonyl; (5) thio urethane type protecting groups such as phenylthiocarbonyl; (6) alkyl type protecting groups as illustrated by triphenylmethyl (trityl); (7) trialkylsilane groups such as timethylsilane. The preferred α-amino protecting group is tert-butyloxycarbonyl.

Protection for the carboxy group of aspartic and glutamic acid is any ester or anhydride which is not removed during removal of the α-amino protecting groups. Preferably the benzyl ester is employed to protect the carboxy group.

Protection for the side chain amino group of amino acids such as lysine, may be by tosyl, t-amyloxycarbonyl, t-butyloxycarbonyl, diisopropyloxycarbonyl, benzyloxycarbonyl, halobenzyloxycarbonyl, nitrobenzyloxycarbonyl, and the like, the 2-chlorobenzyloxycarbonyl group being preferred.

In selecting a particular side-chain protecting group to be used in the synthesis of the peptides of this invention, the following rules should be followed: (a) the side-chain protecting group must be stable to the reagent and under the reaction conditions selected for removing the α-amino protecting group at each step of the synthesis, (b) the protecting group must retain its protecting properties (i.e. not be split off under coupling conditions), and (c) the side-chain protecting group must be removable upon the completion of the synthesis containing the desired amino acid sequence under reaction conditions that will not alter the peptide chain.

The following examples illustrate the preparation of L-(5-oxoprolyl)-L-lysyl-L-lysyl-L-α-glutamyl-L-valinamide, diacetate; L-(5-oxoprolyl)-L-lysyl-L-lysyl-L-α-glutamine, diacetate; L-lysyl-L-lysyl-L-α-glutamyl-L-valinamide, triacetate; L-lysyl-L-lysyl-L-aspartyl-L-valinamide, diacetate and L-lysyl-L-lysyl-L-α-glutamyl-L-valine, diacetate.

EXAMPLE 1

L-(5-oxoprolyl)-N$^\epsilon$-2-chlorobenzyloxycarbonyl-L-lysyl-N$^\epsilon$-2-chlorobenzyloxycarbonyl-L-lysyl-O-benzyl-L-glutamyl-L-valyl benzhydrylamine polystyrene amide In a solid phase peptide synthesizer, 6 gm. of benzhydrylamine hydrochloride resin (Bachem) is neutralized twice with 30% triethylamine in methylene chloride for five minutes each and washed successively with methylene chloride (MeCl$_2$) 1 time and twice with dimethylformamide (DMF) and coupled with 3 gm. t-Boc-L-valine, 2 gm. hydroxybenzotriazole and 2 ml. diisopropylcarbodiimide in DMF overnight. After successive washings with DMF (1 time), MeCl$_2$ (2 times), MeOH (1 time) and MeCl$_2$ (3 times) the resin gives a slightly positive ninhydrin test and is washed with 30% triethylamine in DMF (1 time) and DMF (2 times). The resin is recoupled with 3 gm. t-Boc-L-valine, 2 gm. hydroxybenzotriazole and 2 ml. diisopropylcarbodiimide overnight.

After successive washings as before [DMF (1 time), MeCl$_2$ (2 times), MeOH (1 time) and MeCl$_2$ (2 times)] the resin gives a trace positive ninhydrin test and is deprotected for 30 minutes with 50% trifluoroacetic acid in MeCl₂ followed by successive washing with MeCl₂ (1 time), 30% triethylamine in DMF (2 times) and DMF (2 times). The valyl-resin is coupled with 6.7 gm. t-Boc-γ-benzyl-L-glutamic acid, 3 gm. hydroxybenzotriazole and 3 ml. diisopropylcarbodiimide overnight.

After successive washing, as previously, with DMF, MeCl₂, MeOH and MeCl₂ the resin gives a slight positive ninhydrin test, is further washed with 30% triethylamine in DMF (1 time) followed by DMF (2 times) and recoupled with 3.3 gm. t-Boc-γ-benzyl-L-glutamic acid, 1.5 gm. hydroxybenzotriazole and 3 ml. diisopropylcarbodiimide overnight. After the usual washings the resin gives a trace ninhydrin positive reaction and is deprotected with trifluoroacetic acid 30 min. and neutralized and washed as described in the previous deprotection step. The dipeptidyl resin is coupled with 5 gm. t-Boc-ε-2-Cl-carbobenzoxy-L-lysine, 2 gm. hydroxybenzotriazole and 2 ml. diisopropylcarbodiimide overnight.

The peptidyl resin, being ninhydrin negative, is deprotected with trifluoroacetic acid, neutralized and washed as in the previous deprotections and coupled with 5 gm. of t-Boc-ε-2-Cl-carbobenzoxy-L-lysine, 2 gm. hydroxybenzotriazole and 2 ml. diisopropyl-carbodiimide over a weekend. After the usual washings, the peptidyl resin is still ninhydrin positive and is recoupled with 5 gm. t-Boc-ε-2-Cl-carbobenzoxy-L-lysine, 2 gm. hydroxybenzotriazole and 2 ml. diisopropylcarbodiimide in DMF overnight. After the usual washings the peptidyl resin is still slightly ninhydrin positive and is further coupled with 10 g. t-Boc-2Cl-carbobenzoxy-L-lysine, 4 gm. hydroxybenzotriazole and 4 ml. diisopropylcarbodiimide overnight in DMF. After washing in the usual manner the peptidyl-resin is trace ninhydrin positive, is deprotected with trifluoroacetic acid, neutralized and washed as previously and coupled with 6 gm. pyro-L-glutamic acid, 4 gm. hydroxybenzotriazole and 4 ml. diisopropylcarbodiimide in DMF overnight. The peptidyl resin after the usual washings is still slightly ninhydrin positive and so is recoupled with 6 gm. pyro-L-glutamic acid, 4 gm. hydroxybenzotriazole and 4 ml. diisopropylcarbodiimide in DMF overnight. A second recoupling with the same reagents is necessary to obtain a peptidyl-resin which is trace ninhydrin positive. After washing with ethyl ether and drying the weight is 8 gm.

EXAMPLE 2

L-(5-oxoprolyl)-L-lysyl-L-lysyl-L-α-glutamyl-L-valinamide, diacetate salt

8 Grams of the peptidyl-resin of the previous example is cleaved and deprotected with HF in the presence of 8 ml. of anisole for 1 hour at 0° C., the HF removed in vacuo and the residue washed 3 times with ethyl ether, dried in a current of nitrogen and triturated with 150 ml. of 0.2 N HOAc for five minutes and filtered. The filtrate is lyophylized giving 222 mg. of crude pGlu-Lys-Lys-Glu-Val-NH₂ . 2 HOAc.

150 mg. of crude peptide is chromatographed on Sephadex G-10 using 0.2 N-acetic acid as solvent, and 1 ml. fractions are collected at a flow rate of 15 ml. per hour. Collected fractions 53–63 are combined on the basis of TLC silica gel (Merck), BAW system using ninhydrin and peptide-chlorine spray for detection (R_f 0.06) and lyophylized to yield 67 mg. of the title compound.

Amino acid analysis of the product gave the following: Glu 2.2, Lys 2.1, Val 1.0, NH₃ 1.1.

EXAMPLE 3

L-(5-oxoprolyl)-N^ε-2-chlorobenzyloxycarbonyl-L-lysyl-N^ε-2-chlorobenzyloxycarbonyl-L-lysyl-O-benzyl-L-glutamyl-benzhydrylamine polystyrene amide In a solid phase peptide synthesizer, 7 gms. of benzhydrylamine hydrochloride resin (Bachem) is neutralized twice for five minutes each with 30% triethylamine in methylene chloride and washed successively with methylene chloride (1 time) and DMF (2 times) followed by coupling with 10 gm. t-Boc-γ-benzyl-L-glutamic acid, 4 gms. hydroxybenzotriazole and 4 ml. diisopropylcarbodiimide in DMF overnight. The resin after successive washings with DMF (1 time), MeCl₂ (2 times), MeOH (1 time) and MeCl₂ (2 times) is slightly ninhydrin positive and is recoupled with 10 gm. t-Boc-γ-benzyl-L-glutamic acid, 4 gms. hydroxybenzotriazole and 4 ml. diisopropylcarbodiimide overnight.

After successive washings as before, the resin gives a positive trace ninhydrin test and is deprotected with 50% trifluoroacetic acid in MeCl₂ (containing 0.5% DTE) for 30 minutes followed by washing once with MeCl₂, 30% triethylamine in DMF (2 times) and DMF (2 times). The glutamyl-resin is coupled with 10 gms. t-Boc-ε-Cl carbobenzoxy-L-lysine, 4 gms. hydroxybenzotriazole, and 4 ml. diisopropylcarbodiimide in DMF overnight. After washing successively with DMF, MeCl₂, MeOH and MeCl₂ as before, the resin is ninhydrin trace positive and is deprotected with trifluoroacetaic acid as before. After washing and neutralizing as previously described for this step, the dipeptidyl resin is coupled with 10 grams t-Boc-ε-Cl-carbobenzoxy-L-lysine, 4 grams hydroxybenzotriazole and 4 ml. diisopropylcarbodiimide. After washing as usual, the resin is ninhydrin trace positive, is deprotected with trifluoroacetic acid, washed, neutralized with triethylamine and washed as previously described at this stage, then coupled with 6 gms. pyro-L-glutamic acid, 4 gms. hydroxybenzotriazole and 4 ml. diisopropylcarbodiimide overnight. After washing, the resin is still slightly ninhydrin positive and is recoupled with 6.5 gm. pyroglutamic acid, 4 gm. hydroxybenzotriazole and 4 ml. diisopropylcarbodiimide as usual. After the usual washing at this stage a slightly ninhydrin positive test is obtained for the peptidyl-resin and it is washed once with ether and dried in vacuo for cleavage.

EXAMPLE 4

L-(5-oxoprolyl)-L-lysyl-L-lysyl-L-α-glutamine, diacetate salt

The protected peptidyl resin of Example 3 is deprotected and cleaved with HF in the presence of 8 ml. of anisole, for 1 hour at 0° C. and the HF removed in vacuo overnight. The residue is washed three times with ethyl ether, dried in a current of nitrogen and triturated with 150 ml. of 0.2 N HOAc for five minutes and filtered. The filtrate is lyophylized giving 1.65 gm. of crude pGlu-Lys-Lys-Glu-NH₂. 2 HOAc.

150 mg. of crude peptide acetate is purified on Sephadex G-10 using 0.2 N HOAc as solvent, and 1 ml. fractions are collected at a flow rate of 15 ml. per hour. Tubes 59–63 were combined on the basis of TLC silica gel (Merck), nBuOH, HOAc, H₂O 4:1:5 system using ninhydrin and peptide-chlorine spray for detection (R$_f$0.0) and lyophylized to yield 63 mg. of the title compound.

Amino acid analysis of the product gave the following: Lys, 0.97, Glu 1.0.

EXAMPLE 5

N$^\epsilon$-2-Chlorobenzyloxycarbonyl-L-lysyl-N$^\epsilon$-2-chlorobenzyloxycarbonyl-L-lysyl-O-benzyl-L-glutamyl-L-valyl benzhydrylamine polystyrene amide In a solid phase peptide synthesizer, 6 gm. of benzhydrylamine resin (Bachem) is neutralized twice with 30% triethylamine in MeCl$_2$ for 5 minutes each and washed once with MeCl$_2$ and twice with DMF followed by coupling with 6 gm. t-Boc-L-valine, 4 gm. hydroxybenzotriazole and 4 ml. diisopropylcarbodiimide in DMF for 15 hours. After washing with DMF (1 time), MeCl$_2$ (2 times), MeOH (1 time) and MeCl$_2$ (3 times) the resin is slightly ninhydrin positive and is recoupled with 6 gm. t-Boc-L-valine, 4 gm. hydroxybenzotriazole and 4 ml. diisopropylcarbodiimide for 15 hours. The washing procedure is repeated and the resin again found to be slightly ninhydrin positive. It is recoupled a second time with 6 gm. t-Boc-L-valine, 4 gm. hydroxybenzotriazole and 4 ml. diisopropylcarbodiimide for 15 hours. After the previously described washing, the resin is ninhydrin negative, is deprotected with trifluoroacetic acid for 30 minutes followed by washing once with MeCl$_2$, twice with 30% triethylamine in DMF and twice with DMF. It is coupled with 10 gm. t-Boc-$\gamma$-benzyl-L-glutamic acid, 4 gm. hydroxybenzotriazole and 4 ml. diisopropylcarbodiimide over 15 hours. After the previously described washing procedure the peptidyl resin is ninhydrin negative, and is deprotected with trifluoroacetic acid as previously described. After washing with triethylamine in DMF and with DMF as previously described the peptidyl-resin is coupled with 10 gm. t-Boc-$\epsilon$-Cl-carbobenzoxy-L-lysine, 4 gm. hydroxybenzotriazole and 4 ml. diisopropylcarbodiimide for 15 hours. After the usual washing, the peptidyl-resin is ninhydrin negative and is deprotected with trifluoroacetic acid as described previously, washed in the usual way at this stage and coupled with 10 gm. t-Boc-$\epsilon$-Cl-carbobenzoxy-L-lysine, 4 gm. hydroxybenzotriazole and 4 ml. of diisopropylcarbodiimide as usual. After washing in the usual fashion, the peptidyl resin is ninhydrin negative, is washed with diethylether and dried in vacuo.

EXAMPLE 6

L-lysyl-L-lysyl-L-glutamyl-L-valineamide, triacetate salt

The protected resin of Example 5 is deprotected and cleaved from the resin with HF in the presence of 8 ml. of anisole for 1 hour at 0° C., and the excess HF removed in vacuo. The residue is washed 3 times with ethyl ether, dried in a current of nitrogen, triturated with 150 ml. 0.2 N acetic acid 10 minutes, filtered and the filtrate lyophylized, giving 719 mg. of crude H-Lys-Lys-Glu-Val-NH$_2$. 3 HOAc. 105 mg. of crude peptide is chromatographed on Sephadex G-10 using p.2 N-acetic acid as solvent and collecting 1 ml. fractions at a flow rate of 15 ml. per hour. Tubes 52–57 were combined on the basis of TLC silican gel (Merck) BAW System using ninhydrin detection (R$_f$0.0) and lyophylized to yield 54 mg. of the title compound.

Amino acid analysis of the product gave the following Glu 1.0, Lys 1.97, Val 0.98.

EXAMPLE 7

L-Lysyl-L-lysyl-L-aspartyl-L-valinamide, diacetate salt

Following the procedure of Example 1, there is prepared the intermediate N$^\alpha$-t-butyloxycarbonyl-N$^\epsilon$-2-chlorobenzyloxycarbonyl-L-lysyl-N$^\epsilon$-2-chlorobenzyloxycarbonyl-L-lysyl-$\alpha$-benzyl-L-aspartyl-L-valyl-benzhydrylamine polystyrene amide. Following the procedure of Example 2 and based on the TLC silica gel BAW System using ninhydrin detection (R$_f$0.05), the crude peptide is chromatographed on Sephadex G-10, and the collected fractions are lyophilized to yield 115 mg. of the title compound.

Amino acid analysis of the product gave the following: Val 1.0; Lys 2.1, Asp 1.1, NH$_3$ 1.0.

EXAMPLE 8

L-Lysyl-L-lysyl-L-glutamyl-L-valine, diacetate salt

Following the procedures of Example 1 and using a chloromethylated polystyrene resin, there is prepared the intermediate N$^\alpha$-t-butyloxycarbonyl-N$^\epsilon$-2-chlorobenzyloxycarbonyl-L-lysyl-N$^\epsilon$-2-chlorobenzyloxycarbonyl-L-lysyl-O-benzyl-L-glutamyl-L-valyl hydroxymethyl polystyrene ester. Following the procedure of Example 2 and based on the TLC silica gel BAW System using ninhydrin detection (R$_f$ 0.03), the crude peptide is chromatographed on Sephadex G-10, and the collected fractions are lyophilized to yield 70 mg of the title compound.

Amino acid analysis of the product gave the following: Lys 2.0, Glu 1.0, Val 1.0.

EXAMPLE 9

The activity of the compounds of Examples is determined according to the following procedure:

T lymphocytes are isolated from spleens of male CBA/J or NZB mice. Cell homogenates are prepared in Hank's balanced salt solution (HBSS). After removal of larger particles and repeated washing of the cells in HBSS they are suspended in minimum essential medium (MEM) and passed through a glass wool column to remove macrophages. The cells are then incubated on a nylon wool column at 37° C., 95% air, 5% CO$_2$, for 45 minutes. The non-adherant T lymphocytes are then eluted from the column, counted, and adjusted to 20×10$^6$ cells/ml. 50 µl. of cells are cultured (37° C., 95% air, 5% Co$_2$) with compound, for 48 hours before addition of 0.5 µCi. of 3H-thymidine for the last 16 hours of culture. The total volume of the culture system is 200 µl. The cells are then harvested on a multiple automatic sample harvester (Mash II), the glass fiber filter disks placed in 10 ml. of xylene base scintillation fluid, and counted for 1 minute in a liquid scintillation counter. Results are reported as CPM±SE. Levamisole is used as the standard. Comparisons are made between counts obtained with control cultures and cultures containing compound and a determination made as to whether the compounds are active at the dosage tested. The findings are summarized in Table 1.

TABLE 1

| Compound | Concentration (ng/culture) | N* | $^3$H—Thymidine Uptake CPM + S.E. | P |
|---|---|---|---|---|
| Control | — | 7 | 49,519 ± 4048 | |
| Levamisole | 5 | 8 | 70,353 ± 1561 | <0.05 |
| p-Glu—Lys—Lys—Glu—Val—NH$_2$ | 0 | 10 | 9,876 ± 951 | |

TABLE 1-continued

| Compound | Concentration (ng/culture) | N* | ³H—Thymidine Uptake CPM + S.E. | P |
|---|---|---|---|---|
|  | 1.5 | 5 | 23,736 ± 3417 | <0.01 |
|  | 6.0 | 5 | 31,236 ± 2004 | <0.01 |
|  | 25.0 | 5 | 26,026 ± 3537 | <0.01 |
|  | 100.0 | 5 | 27,830 ± 1749 | <0.01 |
| H—Lys—Lys—Glu—Val—NH₂ | 0 | 7 | 49,519 ± 4048 |  |
|  | 1.5 | 3 | 72,713 ± 3633 | <0.01 |
|  | 6.0 | 4 | 77,979 ± 3760 | <0.05 |
|  | 25.0 | 3 | 62,712 ± 6004 | N.S. |
|  | 100.0 | 4 | 51,021 ± 5527 | N.S. |
| p-Glu—Lys—Lys—Glu—NH₂ | 0 | 7 | 49,519 ± 4048 |  |
|  | 1.5 | 3 | 73,407 ± 3333 | <0.05 |
|  | 6.0 | 3 | 78,727 ± 7102 | <0.05 |
|  | 25.0 | 4 | 73,932 ± 6944 | <0.05 |
|  | 100.0 | 3 | 67,489 ± 5190 | N.S. |
| H—Lys—Lys—Glu Val—OH | 0 | 10 | 2,789 ± 148 |  |
|  | 2.5 | 5 | 3,931 ± 140 | <0.05 |
|  | 10 | 5 | 3,745 ± 172 | <0.05 |
|  | 25 | 5 | 4,397 ± 346 | <0.05 |
|  | 100 | 4 | 4,235 ± 284 | <0.05 |

*— N equals number of animals

The results show that the peptides of the invention have marked activity in stimulating the proliferation of T-cells at very low concentration levels.

What is claimed is:

1. A polypeptide having the following formula:

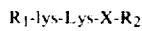

wherein $R_1$ is hydrogen or p-Glu; X is Glu or Asp; and $R_2$ is Val, $NH_2$ or Val-$NH_2$; the fully protected peptide-resin intermediates thereof, and pharmaceutically acceptable salts thereof.

2. The compound of claim 1, which is p-Glu-Lys-Lys-Glu-Val-$NH_2$ or a pharmaceutically acceptable salt thereof.

3. The compound of claim 1, which is p-Glu-Lys-Lys-Glu-$NH_2$ or a pharmaceutically acceptable salt thereof.

4. The compound of claim 1, which is H-Lys-Lys-Glu-Val-$NH_2$ or a pharmaceutically acceptable salt thereof.

5. The compound of claim 1, which is H-Lys-Lys-Glu-$NH_2$ or a pharmaceutically acceptable salt thereof.

6. The compound of claim 1, which is H-Lys-Lys-Asp-Val-$NH_2$ or a pharmaceutically acceptable salt thereof.

7. The compound of claim 1, which is H-Lys-Lys-Glu-Val or a pharmaceutically acceptable salt thereof.

8. A compound of the formula:

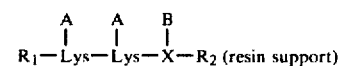

wherein $R_1$ is hydrogen or p-Glu; X is Glu or Asp; and $R_2$ is Val, $NH_2$ or Val-$NH_2$; A is an amino protecting group; and B is a carboxy protecting group.

9. The compound of claim 8, having the formula:

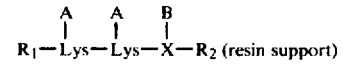

wherein A is 2-chlorobenzyloxycarbonyl; and B is benzyl.

* * * * *